United States Patent
Stawski et al.

(10) Patent No.: US 8,431,150 B2
(45) Date of Patent: *Apr. 30, 2013

(54) BREATH FRESHENING CONFECTIONERY PRODUCTS AND METHODS OF MAKING AND USING SAME

(75) Inventors: Barbara Z. Stawski, Forest Park, IL (US); Thomas M. Mindak, Itasca, IL (US); Philip M. Soukup, Freiburg (DE); Gordon N. McGrew, Evanston, IL (US); James C. Clark, St. Louis, MO (US); Michael S. Haas, Naperville, IL (US)

(73) Assignee: Wm. Wrigley Jr. Company, Chicago, IL (US)

( * ) Notice: Subject to any disclaimer, the term of this patent is extended or adjusted under 35 U.S.C. 154(b) by 1164 days.

This patent is subject to a terminal disclaimer.

(21) Appl. No.: 11/349,526

(22) Filed: Feb. 6, 2006

(65) Prior Publication Data

US 2007/0054014 A1 Mar. 8, 2007

Related U.S. Application Data

(60) Provisional application No. 60/650,786, filed on Feb. 7, 2005.

(51) Int. Cl.
*A61K 9/68* (2006.01)
*A61K 9/20* (2006.01)
*A23G 1/05* (2006.01)

(52) U.S. Cl.
USPC ............................. 424/440; 424/464; 426/660

(58) Field of Classification Search .................. 424/440, 424/464; 426/660
See application file for complete search history.

(56) References Cited

U.S. PATENT DOCUMENTS

| | | | |
|---|---|---|---|
| 2,106,097 | A | 1/1938 | Homan |
| 2,312,381 | A | 3/1943 | Bickenheuser |

(Continued)

FOREIGN PATENT DOCUMENTS

| | | |
|---|---|---|
| DE | 102 61 700 A1 | 7/2004 |
| EP | 0 481 940 A | 4/1992 |

(Continued)

OTHER PUBLICATIONS

Firmenich, Delivery Systems, retrieved from http://www.firmenich.com/portal/page?_pageid=614,143034&_dad=portal&_schema=PORTAL &sid=ds& . . . on Mar. 25, 2004.

(Continued)

*Primary Examiner* — Aradhana Sasan
(74) *Attorney, Agent, or Firm* — Steven P. Shurtz; Brinks Hofer Gilson & Lione

(57) ABSTRACT

A confectionery product comprises a first side and a second side generally opposite to said first side, and a product thickness. The second side comprises an abrasive surface that is suitable for cleaning the top surface of a tongue within an oral cavity. The second side has a width and a length, the smallest of which is at least 1.6 times the product thickness. The product does not include a handle and the product does not include a combination of a soft confectionery with a hard confectionery. In some embodiments the first side is smooth, and may be domed shaped and generally fit the roof of the mouth. The abrasive surface may be provided by 1) a formed, uneven surface, 2) including abrasive particles in the composition making up the second surface, or 3) a combination of a formed, uneven surface and abrasive particles. The confectionery product may be a hard confectionery, but may also be a chewing gum product.

50 Claims, 6 Drawing Sheets

U.S. PATENT DOCUMENTS

| | | | |
|---|---|---|---|
| 2,987,445 A | 6/1961 | Levesque | |
| 3,048,526 A | 8/1962 | Boswell | |
| 4,112,066 A * | 9/1978 | Hussein | 424/48 |
| 4,263,328 A | 4/1981 | Parada et al. | |
| D285,490 S | 9/1986 | Tovey | |
| 4,692,339 A | 9/1987 | Stetson et al. | |
| 4,804,548 A | 2/1989 | Sharma et al. | |
| 4,847,090 A | 7/1989 | Della Posta et al. | |
| 5,462,760 A | 10/1995 | Serpelloni et al. | |
| 5,786,017 A | 7/1998 | Blake et al. | |
| 6,004,334 A | 12/1999 | Mythen | |
| 6,030,605 A | 2/2000 | D'Ameila et al. | |
| 6,083,235 A | 7/2000 | Wagner | |
| 6,083,527 A | 7/2000 | Thistle | |
| 6,161,260 A | 12/2000 | Flewitt | |
| 6,280,762 B1 * | 8/2001 | Bealin-Kelly et al. | 424/440 |
| D464,786 S | 10/2002 | Stanton | |
| 6,582,731 B1 | 6/2003 | Kaufmann | |
| D477,866 S | 7/2003 | Dubois et al. | |
| 6,607,771 B2 | 8/2003 | Benczedi et al. | |
| D509,942 S | 9/2005 | Connolly et al. | |
| 7,063,858 B2 | 6/2006 | Saniez et al. | |
| 7,090,687 B1 | 8/2006 | Gwen | |
| 2002/0132000 A1 | 9/2002 | Saniez | |
| 2002/0198552 A1 | 12/2002 | Yavitz | |
| 2003/0007997 A1 * | 1/2003 | Lawlor | 424/440 |
| 2003/0152668 A1 | 8/2003 | Griffin | |
| 2003/0163149 A1 | 8/2003 | Heisinger | |
| 2003/0224090 A1 | 12/2003 | Pearce et al. | |
| 2004/0156794 A1 | 8/2004 | Barkalow et al. | |
| 2006/0193909 A1 * | 8/2006 | Stawski et al. | 424/464 |
| 2007/0166430 A1 * | 7/2007 | Stawski et al. | 426/3 |
| 2007/0181185 A1 | 8/2007 | Clark | |

FOREIGN PATENT DOCUMENTS

| | | |
|---|---|---|
| EP | 0 267 160 A | 5/1998 |
| EP | 1 214 892 B1 | 6/2002 |
| EP | 1 222 860 A2 | 7/2002 |
| JP | 1997-25221 | 1/1997 |
| WO | WO 91/07100 A1 | 5/1991 |
| WO | WO 01/35764 A1 | 5/2001 |
| WO | WO 2005/102066 A2 | 11/2005 |

OTHER PUBLICATIONS

Firmenich, Polymer Science, retrieved from http://www.firmenich.com/portal/page?_pageid=1295,189627&_dad=portal&_schema=PORTAL&sid=ps . . . on Mar. 25, 2004.

Image of Life Savers wintergreen mint, on sale prior to Apr. 20, 2004.

Wrigley's Eclipse breath mints on sale before Feb. 7, 2004.

Lees et al., Sugar Confectionery and Chocolate Manufacture, Leonard Hill, pp. 165, 183, 184 (1973).

* cited by examiner

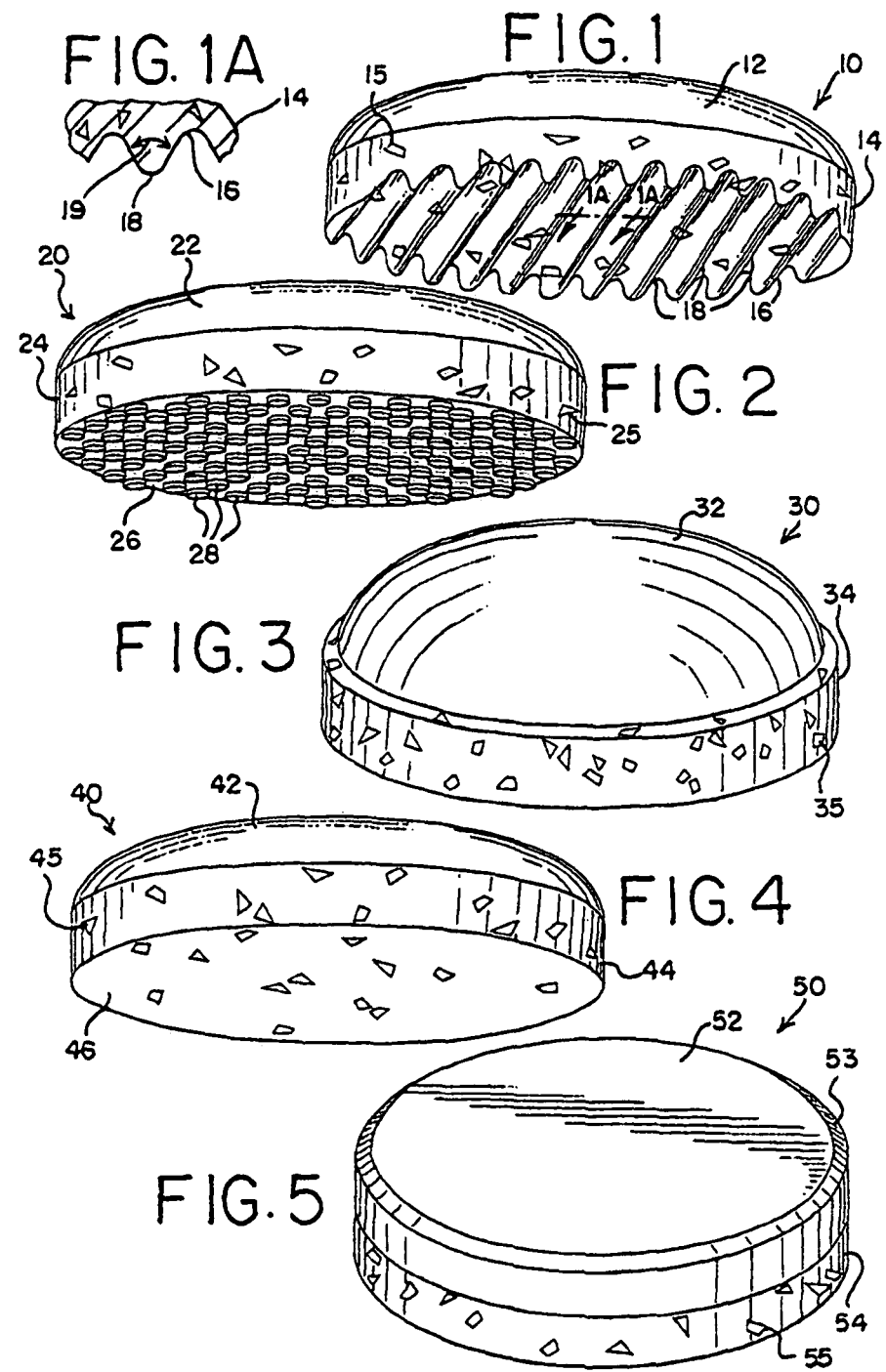

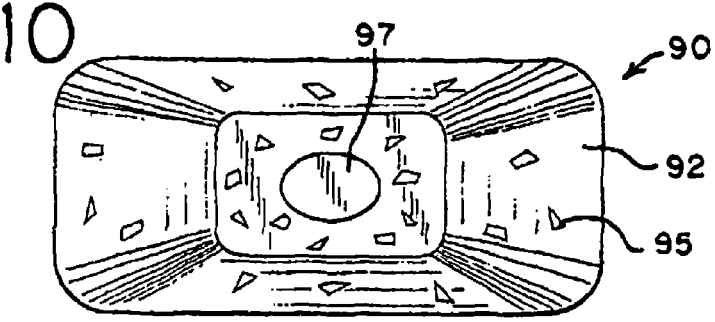
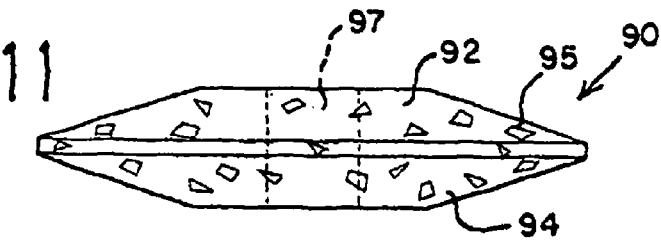
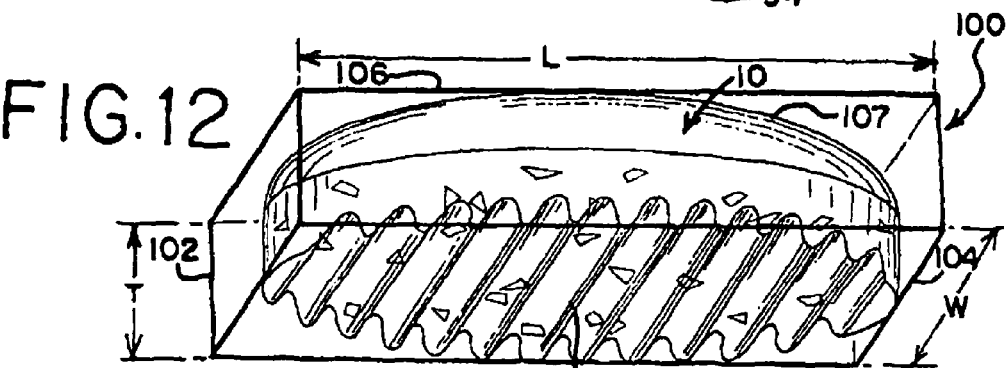
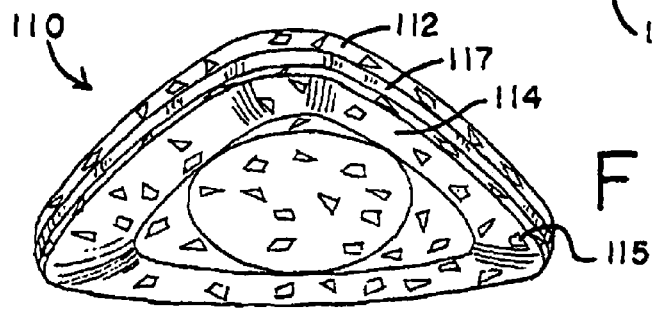
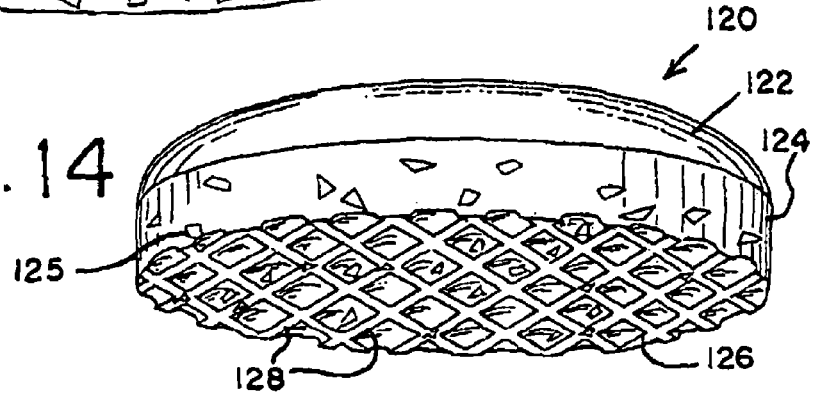

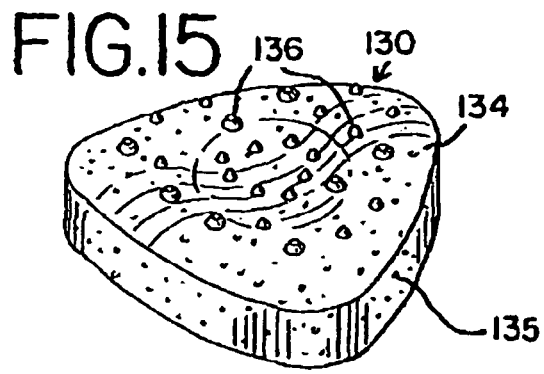
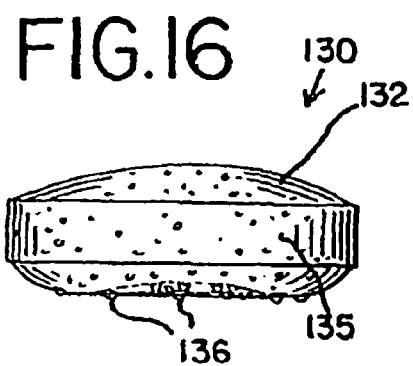
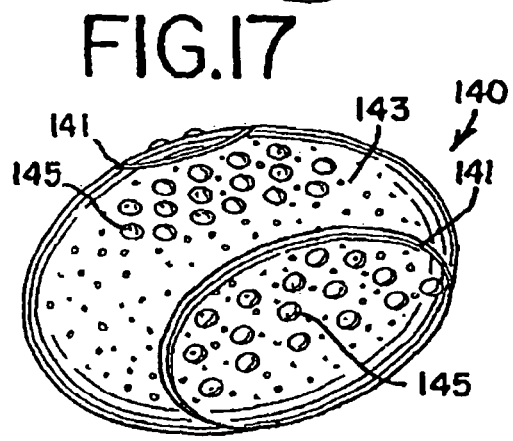
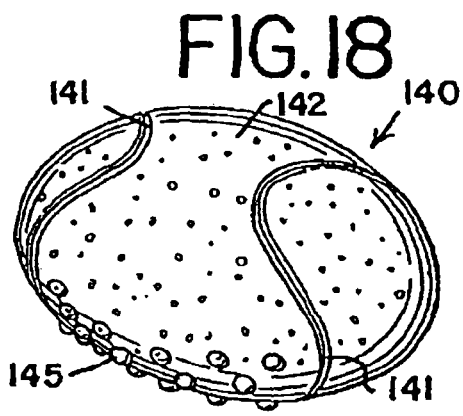
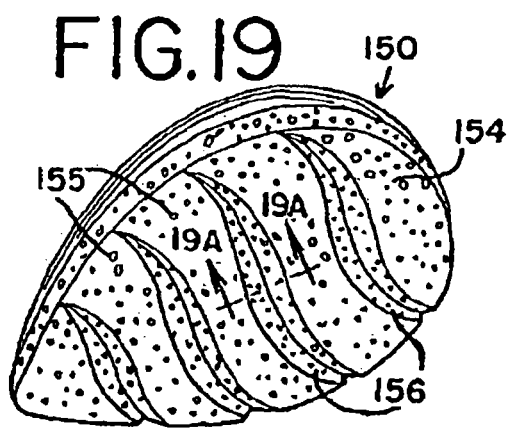
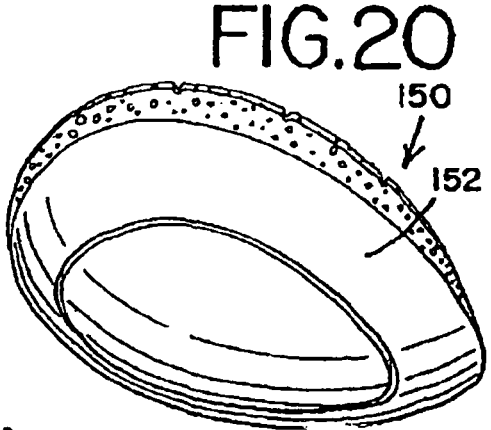
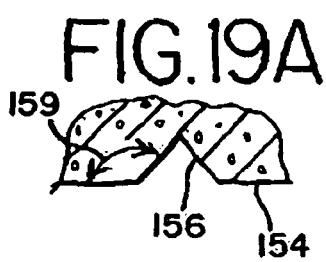

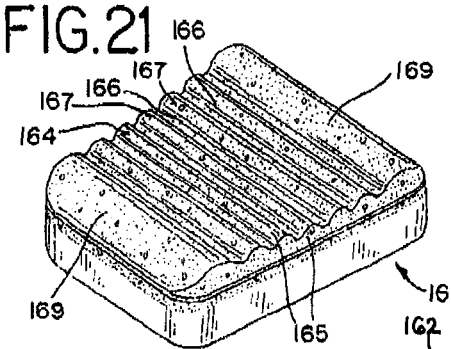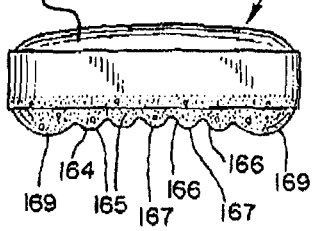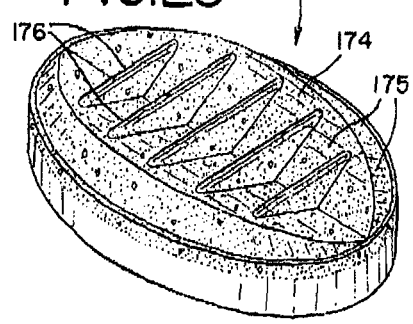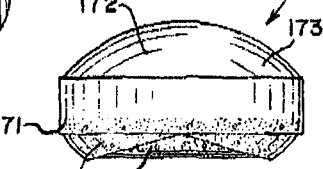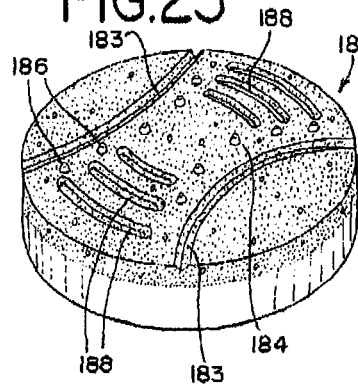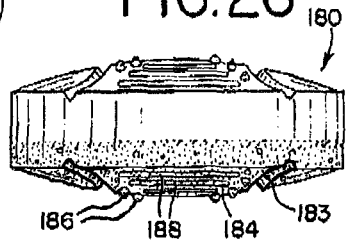

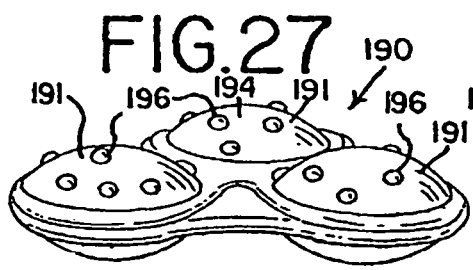
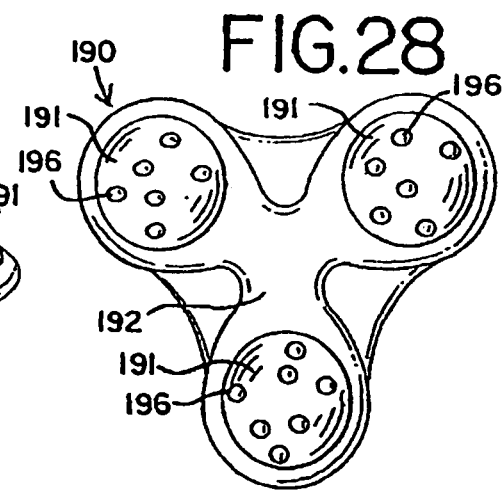
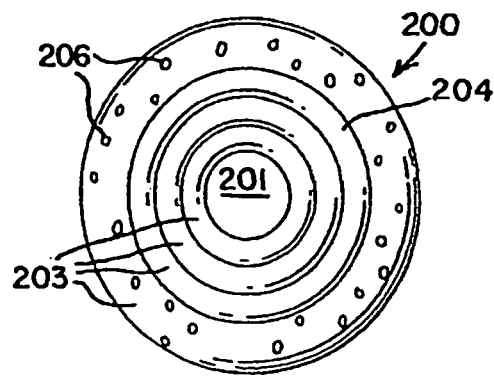
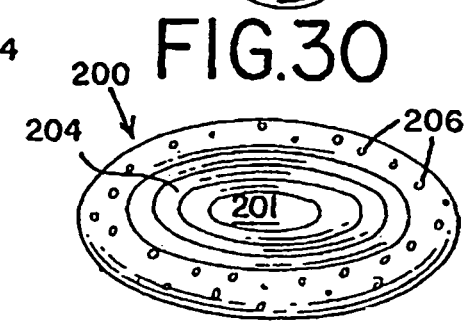

BREATH FRESHENING CONFECTIONERY PRODUCTS AND METHODS OF MAKING AND USING SAME

REFERENCE TO EARLIER FILED APPLICATION

The present application claims the benefit under 35 U.S.C. §119(e) of Provisional U.S. Patent Application Ser. No. 60/650,786, filed Feb. 7, 2005; which is hereby incorporated by reference in its entirety.

BACKGROUND

The present invention relates to confectionery products having breath freshening attributes, particularly pressed tablets, deposited hard candy and tablet chewing gum, and methods of producing and using such confectionery products. More particularly, the invention relates to confectionery products having an abrasive surface that is suitable for scrubbing the top surface of the human tongue and having a width that is at least 1.6 times the thickness of the product.

The existence of bad breath has long been a serious problem. Mouth odor is embarrassing at the least, and may diminish personal interactions. The reasons for its occurrence have not been fully understood, and there have been many attempts to overcome its effects. Plaque formed on the tongue is believed to be a major contributor to bad breath.

Various devices and products have been devised for cleansing the mouth and freshening the breath, notably the toothbrush, dental floss, mouthwash, aromatic candies, and toothpick. However, each of these has disadvantages.

Breath-freshening candies have the disadvantage of merely masking the odor, and not actually removing or breaking down odor-causing particles. Most of the consumer mass-marketed breath-freshener products (gums, mints, rinses, pastes, and strips) do not eliminate the source of bad breath, they just mask breath problems. Other products, and mechanical scrubbing devices, have also been proposed.

Even with these many products there is still room for improvement. For example, a product which is spherical, or otherwise has a thickness that is nearly as great as its width, has a hard time being used to scrape the surface of the tongue because the product rolls around in the mouth instead of staying in one place while the tongue scrapes against it. Life Saver® pressed mints are not sold as a breath-freshening product, and the mints cannot be used to scrape the tongue because surface lettering on the mints is not high enough to provide sufficient tongue cleaning before the lettering is eroded. The use of a lollipop for scrubbing the tongue has the disadvantage that it cannot be done very discretely, as the handle has to be manipulated and protrudes out of the mouth. A product that is made out of a combination of a soft candy material and a hard candy material is more difficult and costly to produce and package than a product that is either completely hard or soft. Thus there is still a need for an easily produced product which can be used to discretely scrub the tongue and reduce or remove tongue plaque, yet still be enjoyed as a confectionery. Therefore, the need exists for a product and method of freshening breath that is safe, portable, discrete and effective.

BRIEF SUMMARY OF THE INVENTION

Confectionery products have been invented that can be discretely used to scrub the tongue, thereby providing breath freshening and other oral health benefits.

In a first aspect, the invention is a confectionery product for use in cleaning the surface of a human tongue comprising: a first side and a second side generally opposite to said first side, and a product thickness; the second side comprising an abrasive surface that is suitable for cleaning the top surface of a tongue within an oral cavity; and the second side having a width and a length, the smallest of which is at least 1.6 times the product thickness. The product is formed and consumed without using a handle. Further, the product does not include a combination of a soft confectionery with a hard confectionery.

In a second aspect, the invention is a method of removing bacteria from the top surface of a human tongue comprising placing a confectionery product having a first side and a second side generally opposite to said first side, and a product thickness, in an oral cavity, the second side comprising an abrasive surface and having a width and a length, the smallest of which is at least 1.6 times the product thickness, with the abrasive surface contacting the top surface of the tongue; and causing the abrasive surface of the confectionery product to be scraped across the top surface of the tongue while the oral cavity is closed to thereby loosen bacteria on the top surface of the tongue. The product does not include a handle and the product does not include a combination of a soft confectionery with a hard confectionery.

Some embodiments have a smooth surface on one side and an abrasive surface on the other side. The smooth surface can be held against the roof of the mouth while the tongue scrubs across the abrasive surface. The term "abrasive" means that the surface is effective, either immediately when placed in the mouth or after starting to be dissolved, to remove odor causing deposits on the tongue. Of course the abrasive surface may also be suitable to clean other soft oral surfaces, such as the inside of the cheek. The term "smooth" means that the surface, even after being partially dissolved, does not cause irritation against the gums or roof of the mouth. Some confectionery products of the present invention are completely hard confectionery products, which mean that they retain their shape in the mouth and slowly dissolve. These products are primarily consumed by sucking, and will generally shatter if bitten sufficiently hard. The confectionery products may also include chewing gum products, including tablet chewing gum.

Other aspects of the invention may combine two or more of the features from any of the foregoing aspects of the invention.

Embodiments of the invention provide a confectionery product that can be placed in the mouth and discretely used to scrub the tongue and remove particles of food and bacteria. The dimensions of the product make it less prone to rolling around in the mouth and therefore more useable as a tongue scrubber. The domed shape of some embodiments fits into the roof of the mouth, or a concave shape can be used to form a vacuum, to hold the confectionery product in place while the tongue is scrubbed across its lower surface. The top surface may be smooth so as to not cause irritation in the mouth. The confectionery products have an advantage that they may be completely consumed. These and other advantages of embodiments of the invention will be best understood in light of the attached drawings.

BRIEF DESCRIPTION OF THE DRAWINGS

FIG. 1 is a bottom perspective view of a first embodiment of a confectionery product of the present invention.

FIG. 1A is a cross-sectional view taken along line 1A-1A of FIG. 1.

FIG. 2 is a bottom perspective view of a second embodiment of a confectionery product of the present invention.

FIG. 3 is a top perspective view of a third embodiment of a confectionery product of the present invention.

FIG. 4 is a bottom perspective view of a fourth embodiment of a confectionery product of the present invention.

FIG. 5 is a top perspective view of a fifth embodiment of a confectionery product of the present invention.

FIG. 10 is a top plan view of a ninth embodiment of a confectionery product of the present invention.

FIG. 11 is a side elevational view of the confectionery product of FIG. 10.

FIG. 12 is a bottom perspective view of the product of FIG. 1 showing an imaginary box that may be used to determine the dimensions of a product.

FIG. 13 is a bottom perspective view of a tenth embodiment of a confectionery product of the present invention.

FIG. 14 is a bottom perspective view of an eleventh embodiment of a confectionery product of the present invention.

FIG. 15 is a bottom perspective view of a twelfth embodiment of a confectionery product of the present invention.

FIG. 16 is a side elevational view of the product of FIG. 15.

FIG. 17 is a bottom perspective view of a thirteenth embodiment of a confectionery product of the present invention.

FIG. 18 is a top plan view of the product of FIG. 17.

FIG. 19 is a bottom perspective view of a fourteenth embodiment of a confectionery product of the present invention.

FIG. 19A is a cross-sectional view taken along line 19A-19A of FIG. 19.

FIG. 20 is a side elevational view of the product of FIG. 19.

FIG. 21 is a bottom perspective view of a fifteenth embodiment of a confectionery product of the present invention.

FIG. 22 is a side elevational view of the product of FIG. 21.

FIG. 23 is a bottom perspective view of a sixteenth embodiment of a confectionery product of the present invention.

FIG. 24 is a side elevational view of the product of FIG. 23.

FIG. 25 is a bottom perspective view of a seventeenth embodiment of a confectionery product of the present invention.

FIG. 26 is a side elevational view of the product of FIG. 25.

FIG. 27 is a bottom perspective view of an eighteenth embodiment of a confectionery product of the present invention.

FIG. 28 is a bottom plan view of the product of FIG. 27.

FIG. 29 is a bottom plan view of a nineteenth embodiment of a confectionery product of the present invention.

FIG. 30 is a bottom perspective view of the product of FIG. 29.

DETAILED DESCRIPTION OF THE DRAWINGS AND THE PRESENTLY PREFERRED EMBODIMENTS

Figure 6:
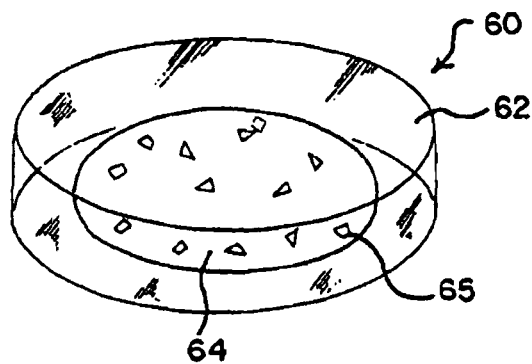
FIG. 6 is a top perspective view of a sixth embodiment of a confectionery product of the present invention.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

There are several presently disclosed embodiments of the invention. Each of the embodiments is common in that they comprise confectionery products that include an abrasive surface and have a width that is at least 1.6 times the product's thickness. Preferably the width is at least 1.7 times the thickness, and more preferably at least 1.8 times the thickness. Most preferably the product will have a width that is at least twice the thickness of the product. Some of the products are made with layers, and made of separate confectionery compositions. The abrasive surface may be provided by abrasive particles, also referred to as inclusions, in the confectionery, or may be provided by a formed, uneven surface, or may have both abrasive inclusions and a formed, uneven surface. The formed surface may be molded using a compression die. When the abrasive surface is a formed, uneven surface, the piece will typically have projections or grooves which expose a defined convex angle of not more than 135 degrees. Alternatively, if the piece comprises inclusions to provide the abrasive surface, the inclusions will typically be hard particles of at least 100 microns, preferably at least 200 microns, and most preferably at least 400 microns in size, and which are less soluble than the surrounding matrix. The inclusions may be present on the surface to begin with, or may be exposed as the product is dissolved in the mouth to produce a perceivably rough surface.

In each instance the abrasive surface is suitable for scrubbing the top surface of the tongue within the oral cavity. The confectionery may be made of a pressed tablet, a deposited hard candy, a tablet chewing gum, or any other type of confectionery that is suitable to provide such an abrasive surface.

The abrasive surface may be provided at least in part by surface features having at least one scraping edge. The at least one scraping edge may be located on a protrusion on the abrasive surface. For example, the scraping edge may be formed by an acute angle on the protrusion. The scraping edge may also be formed on the edge of a groove in the abrasive surface. The abrasive surface may be provided at least in part by surface features comprising either or both projections and grooves, the projections having a height of at least 0.015 inches and the grooves having a depth of at least 0.008 inches. More preferably the surface features will comprise projections having a height of at least 0.018 inches and/or grooves having a depth of at least 0.009 inches. Most preferably the height of the projections will be at least 0.020 inches and/or the depth of the grooves at least 0.010 inches.

Alternatively the at least one abrasive surface may be provided by abrasive particles in the confectionery composition. The abrasive particles may either be incorporated into the composition or located on the abrasive surface of the tablet. Of course the abrasive particles may be embedded in a surface layer making up the abrasive surface of the product.

A first embodiment is shown in FIG. 1. A confectionery product in the form of a pressed tablet 10 has a generally cylindrical shape with two layers, a top layer 12 and a bottom layer 14. The tablet 10 has a first side, formed by a generally domed shape top of the first layer, and a second side 16 generally opposite to the first side. The thickness (height) of the tablet 10 is less than half of the diameter of the cylindrical shape. The second side 16, forming one of the ends of the cylinder, comprises an abrasive surface that is suitable for scrubbing the top surface of the tongue within the oral cavity. In the embodiment of tablet 10, the second side 16 is generally planar with a plurality of raised portions thereon. In this embodiment, the abrasive surface comprises a formed, uneven surface having a washboard shape with ridges 18. The ridges 18 extend away from surface 16 in a triangular fashion, as shown in FIG. 1A. The ridges 18 define projections which expose a convex angle 19. The angle 19 of the sides of the triangle is less than 135 degrees. In addition, the abrasive surface is provided by abrasive inclusions 15 in the composition of the confectionery making up the second layer 14.

The first layer 12 providing the domed surface is made from a first composition that is different than a second composition making layer 14 providing the abrasive surface 16. Both compositions may be confectionery materials. They may differ in many respects, or they may differ only in the fact that the second composition has abrasive inclusions 15 mixed into it. However, as noted earlier, the product will be made without both soft and hard confectionery material together. The first and second compositions may be different in color from one another. For example, the first composition making top layer 12 may be generally white, while the second composition making the second layer 14 may be generally blue.

The first side comprises a non-abrasive, smooth surface. In this embodiment, the dome shape of the top layer 12 is generally shaped to fit the contour of an oral cavity. The interface between the first and second layers is generally parallel to the abrasive surface 16.

FIG. 12 shows an imaginary box 100 drawn around the tablet 10. The product thickness is preferably determined by forming an imaginary three dimensional box having three sets of two parallel sides, each side being at right angles to the other sides to which it is connected. Two of the sides are oriented horizontally, and are considered to be top and bottom sides. The product is oriented in the box such that the center of gravity (assuming the product has a uniform density) of the product is as close as possible to the bottom side. The sides each contact the surface of the product, possibly at multiple points, but do not intersect the product. If the product shape is such that numerous boxes could be drawn satisfying the forgoing, the imaginary box used for determining the product's dimensions is the box that has the smallest volume of any possible box meeting the forgoing criteria. The smallest dimension of the box is considered to be the thickness of the product. The next smallest dimension is considered to be the width of the product, and the largest dimension is considered to be the length of the product. For box 100, the height T of side 102 is the thickness of the tablet 10. The length W of side 104 is the width of the abrasive surface, and the length L of side 106 is the length of the abrasive surface. Where the abrasive surface is not generally planar, the abrasive surface is considered as having a width and length equal to the width and length of the product.

Using the forgoing figure, it can be seen that the tablet 10 has a first side 107 and a second side 109 generally opposite to the first side 107. The product thickness is T. The second side 109 comprises an abrasive surface that is suitable for cleaning the top surface of a tongue within an oral cavity. The second side 109 has a width W and a length L, the smallest of which is at least 1.6 times the product thickness T. It is noted that while generally the abrasive surface will be on the bottom of the aforementioned box, the definition of thickness is not dependent thereon. Using the imaginary box definition of thickness, the thickness of the product is simply the smallest dimension of the imaginary box described above.

FIG. 2 shows another embodiment of the invention, pressed tablet 20, with a first layer 22 made of a first composition providing a non-abrasive surface and a second layer 24 made of a second composition. The second composition provides an abrasive surface 26 generally opposite to the domed upper surface on top layer 22. In this embodiment, in addition to the abrasive inclusions 25, the abrasive surface 26 is unevenly formed with a multitude of small, round protrusions 28.

FIG. 3 shows a pressed tablet 30 again made with two distinct layers, top layer 32 and bottom layer 34. The tablet 30 is different than the tablets 10 and 20 in that the two layers are not the same diameter. In this case, the diameter of the second layer 34 is larger than the diameter of the first layer 32. Abrasive inclusions 35 provide an abrasive surface on the second layer.

The tablet 40 shown in FIG. 4 again has two layers 42 and 44 made of different compositions. While the top layer 42 provides a domed top surface, the abrasive surface 46 in this embodiment is provided solely by the abrasive inclusions 45.

FIG. 5 shows a tablet 50 with a bottom layer 54 that comprises abrasive inclusions 55 providing an abrasive surface on the bottom of the tablet 50. In this embodiment, the top layer 52 has a smooth surface, but instead of being domed the surface is generally flat, with a beveled corner 53 on the end opposite the abrasive surface.

Figure 7:
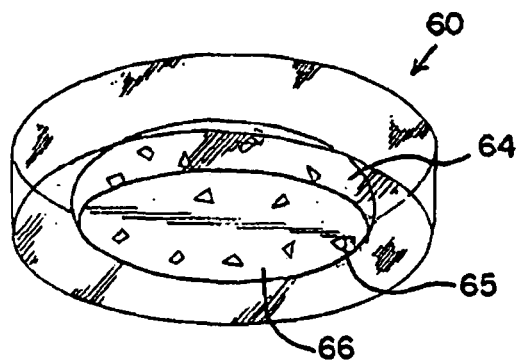
FIG. 7 is a bottom perspective view of the confectionery product of FIG. 6.

The embodiment of FIG. 6 shows a deposited hard candy piece 60. In this embodiment, the candy has a first part 62 made from a first confectionery composition mostly surrounding a second part 64 made from a second confectionery composition different than the first confectionery composition. As seen from the bottom view of FIG. 7, the second part 64 has an exposed surface 66 on the bottom of candy piece 60. Abrasive inclusions 65 in the second composition provide the second part 64 with an abrasive surface that is suitable for scrubbing the top surface of the tongue. The composition of first part 62 may be clear, so that the second part 64 and abrasive inclusions 65 may be seen through the candy. The composition of first part 62 may also be translucently colored.

Figure 8:
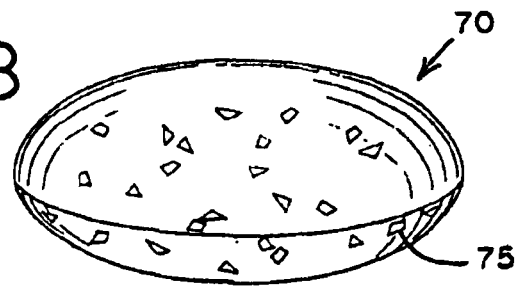
FIG. 8 is a top perspective view of a seventh embodiment of a confectionery product of the present invention.

Pressed tablet 70 shown in FIG. 8 does not have distinct layers, and may be formed all of one composition. The composition comprises abrasive inclusions 75 to provide an abrasive surface opposite the generally domed top surface on the tablet. The abrasive inclusions in this embodiment comprise solid matrices of carbohydrates, solid matrices of polyols, extruded carbohydrates or extruded polyols, and also carry a flavor.

Figure 9:
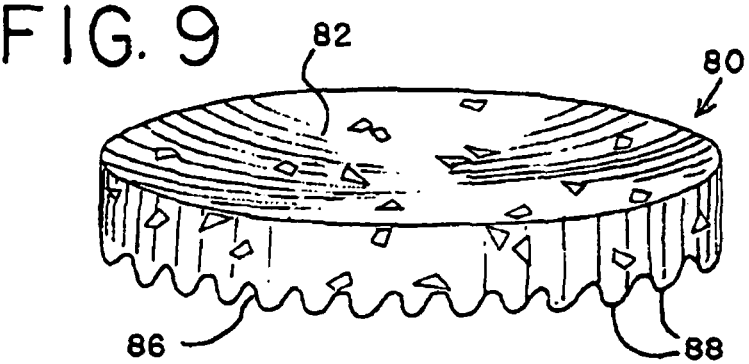
FIG. 9 is a top perspective view of an eighth embodiment of a confectionery product of the present invention.

Pressed tablet 80 shown in FIG. 9 is also made with only a single composition. Rather than having a domed top surface, the top surface 82 of tablet 80 is concave in shape. The opposite, bottom surface 86 is generally planar and has a formed, uneven surface 86 made up of ridges 88 in a washboard pattern. It is believed that a person can suck on the tablet 80 in such a way that a partial vacuum can be formed between the concave surface 82 and the roof of their mouth. This vacuum will then help to hold the tablet 80 in place while the tongue is scrubbed across the abrasive surface 86. The tablet 80 may be oblong rather than round to help fit against the palate.

The embodiment shown in FIGS. 10 and 11 comprises a pressed mint 90 having a center 97 that is a different confectionery composition than the confectionery composition making up the top layer 92 and bottom layer 94. Further, if desired, these two layers may be the same material, and not distinct layers. The composition of the outer shell includes abrasive inclusions 95 and thus provides an abrasive surface, whereas the material making the center 97 may be colored blue or some other color, and include mint flavoring and other breath freshening ingredients.

The tablet 110 in FIG. 13 has a generally triangular shape and three layers. The bottom layer 114, and optionally the top layer 112 as shown in FIG. 13, includes abrasive inclusions 115, while the middle layer 117 contains a breath freshening ingredient and is a different color than layers 112 and 114. Thus, while the top and bottom layer confectionery compositions are both different than the composition of the middle layer confectionery, at least the bottom layer is of a confectionery composition that comprises an abrasive surface suitable for scrubbing the top surface of the tongue.

FIG. 14 shows an embodiment of a pressed tablet 120. The tablet has a top layer 122 made of a first confectionery material and a bottom layer 124 made of a second confectionery material. The second confectionery material comprises abrasive inclusions 125, and is formed with an uneven surface 126. In this embodiment, the ridges 128 form a grid pattern. The abrasive surface is generally planar except for the features making it abrasive.

Another embodiment of a pressed tablet 130 is shown in FIGS. 15 and 16. The tablet 130 has an abrasive bottom surface 134 comprising a plurality of individual bumps 136 protruding from the abrasive surface. The bumps 136 have a plurality of different sizes. The bumps 136 are shown as generally circular, but they could be of other shapes. The top surface 132 does not include bumps. The bottom half of the product includes abrasive inclusions 135. The top surface 132 is generally concave while the bottom surface 134 is generally convex. The bumps 136 and inclusions 135 provide the bottom surface of the pressed tablet 130 with an abrasive surface suitable for cleaning the surface of a human tongue in an oral cavity.

Tablet 140, shown in FIGS. 17 and 18, is elliptical in its major cross-section. The length of the minor axis of the ellipse (product width) is at least 1.6 times the height of the product (its thickness). The outer surface of the shape includes a groove 141 that resembles the joint on the cover of a baseball. The abrasive surface on the bottom of tablet 140 is provided by bumps 145 extending from the lower hemispherical portion of the shape, as well as abrasive inclusions 143 in the material used to form the bottom half of the tablet, and to a small extent the grooves 141. The top surface 142 may include bumps and the grooves 141 as shown, or may be smooth.

Pressed tablet 150 shown in FIGS. 19 and 20 also has a bottom surface 154 with grooves 156. The grooves 156 are wavy, and extend generally parallel to each other across the bottom width of the tablet. As best seen in FIG. 19A, the grooves 156 intersect with the bottom surface 154 to expose a defined convex angle 159 of not more than 135 degrees. The tablet 150 is generally teardrop shaped. The bottom surface 154 also includes abrasive inclusions 155. However, the top surface 152 of the tablet 150 is generally smooth.

FIGS. 21 and 22 show a generally keystone shaped pressed tablet 160. While the top surface 162 is generally smooth, the bottom surface 164 has a plurality of grooves 166 running across the width of the keystone. In this product, the grooves 166 separate humps 167. The humps 167 and abrasive inclusions 165 provide an abrasive surface to the product. The product may be made of two different materials, with the top surface 162 being made of one material that does not contain abrasive inclusions, and the humps 167 being made of another material that does contain the abrasive inclusions 165. The humps 169 on the ends may be larger than the humps 167 in the middle portion of tablet 160.

In the pressed tablet 170 shown in FIGS. 23 and 24, the abrasive surface is provided by a plurality of generally parallel ridges 176 extending generally perpendicular from the bottom side 174 of the tablet 170. The abrasive bottom surface 174 is generally concave except for the features making it abrasive. The top surface 172 is generally smooth. The ridges 176 each have a generally straight outer surface, but in an alternate embodiment (not shown) the ridges could extend further and have a generally arcuate outer surface. The plurality of ridges comprises at least three ridges, more preferably five ridges. In the embodiment show, all of the ridges have the same height, but in an alternate embodiment, the ridges toward the middle of the group of ridges could extend outwardly of the ridges on the sides of the group. The tablet 170 may be made with two layers; the bottom layer 171 forming the ridges 176 and bottom surface 174 may contain abrasive inclusions 175, while the top layer 173 is made without the inclusions.

As shown in FIGS. 25 and 26, another pressed tablet 180 is generally circular in shape in plan view. The abrasive bottom surface 184 comprises a plurality of generally circular bumps 186 and a plurality of curved protrusions 188. Two grooves 183 are also formed in the bottom surface 184. The bumps 186, protrusions 188 and grooves 183 all contribute to providing the bottom of the tablet with an abrasive surface. The top surface 180 may have bumps and protrusions, as shown, or the top of tablet may be smooth.

The tablet 190 shown in FIGS. 27 and 28 is generally triangular in plan view. The shape includes three orbs 191, one at each apex of the triangle. The bottom abrasive surface 194 is provided by inclusions used to make the lower half of the tablet. The inclusions in the bottom surface 192 between the orbs, and particularly in the orbs, provide a surface suitable for scrubbing the tongue.

As shown in FIGS. 29 and 30, the tablet 200 is also generally circular in shape in plan view. The tablet 200 has an open center 201. The tablet comprises a shape depicting a plurality of concentric rings 203. The rings 203 themselves and inclusions 206 contained in the material making up the bottom half of the tablet provide the bottom surface 204 of the tablet 200 with an abrasive surface. The upper surface may be smooth or may express the concentric ring shape.

The product may have a piece weight of between about 1 and about 2 grams. For pressed tablets, the piece weight may be about 1 gram. For deposited hard candy pieces, the weight may be between about 1.5 and about 2 grams. The product thickness may be between about 1/16 and about ½ inch, and will preferably be at least about ⅛ inch. The smallest of the length and width of the product may be between about ¼ and about 1 inch. The greatest of the length and width of the product is typically less than 1½ inches. Often the pieces will be sized so that they have no dimension greater than about 25 mm. For a cylindrical shaped piece with a diameter greater than its height, this means that the diameter will be less than about 25 mm. Most frequently the pieces will be between about 15 and about 20 mm in their longest dimension.

While the figures show several shapes, it is contemplated that other shapes can be used. Further, surface markings may be included on the products, such as a letter or other indicia.

Some confectionery compositions of the present invention will be sugarfree, and may contain one or more antibacterial agents. In addition to, or other than mint flavors, other flavoring agents can be included in the confectionery products. Physiological cooling agents may be included in the products, as well as other ingredients that give a tingling sensation. In the case of products with multiple layers, each layer may have different flavoring agents or levels. In one embodiment, the confectionery product may comprise a coating layer covering at least a portion of the product. In that case, the coating layer may contain flavoring agents at a level higher than any flavoring agents in the remainder of the product.

The particle size of the abrasive inclusions in some embodiments should predominantly be at least 100 microns, with a maximum of 2000 microns (0.1-2 mm). Some abrasive inclusions have a particle size range of about 200 to 600 microns, others are 600 to 1200 microns, and still others may be larger, up to 2000 microns. A preferred range is 200 to 1000 microns. If the abrasive inclusions include a wide range of particle sizes, then the foregoing ranges describe the particle sizes of the majority (from a weight standpoint) of the particles.

The abrasive inclusions may be made from a number of different materials, including crystalline sugars or polyols; solid matrices of carbohydrates, polyols or mixtures; or extruded carbohydrates, polyols, or mixtures; granular food acids; granular inorganic edible salts, such as calcium phosphate salts and other calcium salts including calcium lactate, calcium carbonate and calcium gluconate, silica, silicate salts and bicarbonates; and mixtures thereof On the one hand, solid matrices (such as from fluid bed coating or spray drying) and extruded carbohydrates or polyols are preferred because these inclusions may also contain flavors and/or colors. When the inclusions include colors, the abrasive particles will preferably have a contrasting color from the remainder of the compressible composition into which they are added. On the other hand, some inorganic salts are preferred because they have dental benefits, such as tooth remineralization or whitening. Further, abrasive food acids and bicarbonates may be combined to not only provide an abrasive surface, but to give an effervescent effect when placed in the mouth.

U.S. Pat. No. 5,786,017 discloses particulate flavor compositions. U.S. Pat. No. 6,607,771 discloses granules for the controlled release of volatile compounds. European Patent Application Publication No. EP 1 214 892 discloses a number of moisture and oxygen stable compositions. PCT Patent Publication No. WO 01/35764 discloses a spray-dried composition in a carbohydrate substrate. Materials disclosed in these references that provide an abrasive surface suitable for scrubbing the tongue may be used as abrasive inclusions in the present invention. Each of these documents is hereby incorporated by reference.

The pressed tablet may include one or more of the following: anti-microbial agents; physiological cooling agents; breath freshening agents; breath freshening and mouth odor masking flavors; and dental active agents. Some anti-microbial agents include cardamom oil, magnolia bark extract, cranberry, geraniol, cinnamaldehyde, peppermint, triclosan, chlorhexidine, cetyl pyridinium chloride (CPC) and mixtures thereof Some physiological cooling agents include menthol, N-2,3-trimethyl-2-isopropyl butanamide, 3-1-menthoxypropane-1,2-diol, N-ethyl-p-menthane-3-carboxamide, menthane ketals, menthyl succinate, isopulegol, menthyl glutarate and mixtures thereof Some breath freshening agents include salts of zinc, salts of copper, polyphenols, mushroom extracts and mixtures thereof. Some breath freshening and mouth odor masking flavors include cinnamon, mint, wintergreen, fruit flavors and mixtures thereof. Some dental active agents include tooth whiteners, fluoride, stain removers, calcium salts, phosphate salts and mixtures thereof.

There are different methods of making the different products of the present invention. The tablet chewing gum product can be made from directly compressible chewing gum powder. Such free-flowing powder is a material in which the basic ingredients (such as gum base and a bulk sweetener) have already been mixed. Dry flavors, lake colors, fruit acids, if desired, and some lubricant such as magnesium or calcium stearate, are blended together in a powder blender such as a ribbon blender, V-blender or cone blender. If abrasive inclusions are also added, they are blended in as well. Thereafter a tablet press or a briquetting machine can be used to form the products.

The pressed tablets of the present invention can be made using conventional tablet pressing procedures and equipment. The compressible composition comprises one or more materials selected from the group consisting of sugars and sugar alcohols. The compressible composition may comprise a directly compressible sugar, such as sucrose plus a binder. The binder may comprise corn syrup and/or maltodextrin. The compressible composition may also comprise a directly compressible sugar alcohol. In some embodiments, the sugar alcohol may be sprayed with water before compression.

A process for making two layer boiled hard confectionery products may comprise the steps of producing a first confectionery composition and depositing it in a mold to form a first layer of the confectionery product, the mold creating the abrasive surface on the first layer; and then producing a second confectionery composition and depositing it on the first layer to form a second layer. The second confectionery composition may be deposited at a viscosity and under conditions sufficient to result in the second layer having a domed surface opposite the abrasive surface. The domed surface may be generally shaped to fit the top contour of the oral cavity. This method can thus be used to make products shaped like the tablets shown in FIGS. 1, 2, 4 and 14. Rather than making two separate compositions, one with abrasive inclusions and one without, the abrasive inclusions may be embedded in just one surface as a product is formed. Thus two separate compositions are in the final product, one being the composition as initially produced, and the other being a layer having the same composition but with abrasive inclusions included. In a deposited boiled hard candy, this may be accomplished by placing abrasive inclusions in the bottom of the mold before the boiled hard candy is deposited, or in the bottom of the die before the compressible material is added.

The inventive products can be used to removing bacteria from the top surface of a human tongue. This will generally involve placing the confectionery product having a first side and a second side generally opposite to the first side, and a product thickness, inside the oral cavity. The second side comprises the abrasive surface and has a width and a length, the smallest of which is at least 1.6 times the product thickness, with the abrasive surface contacting the top surface of the tongue. The abrasive surface of the confectionery product is scraped across the top of the tongue, usually while the oral cavity is closed, to thereby loosen bacteria on the top surface of the tongue. Preferably the abrasive surface comprises surface features having at least one scraping edge. Preferably the roof of the oral cavity holds the confectionery product stationary in the oral cavity while the tongue is scraped across the abrasive surface.

The following examples help to explain the invention.

EXAMPLE 1

| Pressed Tablet | |
|---|---|
| First layer | |
| Sorbitol | 97.99% |
| Peppermint flavor | 0.75% |
| Magnesium stearate | 0.64% |
| Encapsulated flavor | 0.28% |
| Menthol | 0.18% |
| Silicon dioxide | 0.16% |
| Total | 100.0 |

EXAMPLE 1-continued

| Pressed Tablet | |
| --- | --- |
| Second layer | |
| Sorbitol | 95.94% |
| Abrasive inclusions | 2.01% |
| Peppermint flavor | 0.75% |
| Magnesium stearate | 0.64% |
| Encapsulated flavor | 0.28% |
| Menthol | 0.18% |
| Blue color | 0.04% |
| Silicon Dioxide | 0.16% |
| Total | 100.0 |

The materials are mixed together as powders. The second layer can be added first to the die formed tablet press and given a precompression. The top or first layer can then be added to the form and the tablet compressed. The blue colored portion with the abrasive inclusions made from an extruded polyol matrix can have the washboard surface formed from the bottom die of the tablet press. The piece size can be 1 gram total, with an equal sized top and bottom layer. The thickness of the product is less than one-half of its width.

EXAMPLE 2

| Boiled Hard Candy | |
| --- | --- |
| First layer | |
| Isomalt | 99.14% |
| Lemon-mint flavor | 0.49% |
| Citric acid | 0.24% |
| Acesulfame/aspartame | 0.13% |
| Total | 100.0 |
| Second layer | |
| Isomalt | 98.62% |
| Abrasive inclusions | 0.51% |
| Lemon-mint flavor | 0.49% |
| Citric acid | 0.24% |
| Blue color | 0.01% |
| Acesulfame/aspartame | 0.13% |
| Total | 100.0 |

The isomalt is a syrup, boiled to about 1-3% moisture. As it cools, the flavor, acid, and sweeteners are added. When the second layer material is being made, the abrasive inclusions compound is also added as the low-moisture isomalt syrup cools. The second layer can be deposited into forms having a washboard surface on the bottom. This second layer will be deposited at a higher temperature to make it less viscous so that it conforms to the washboard surface of the mold. The top or first layer can then be added to the deposit form at a lower temperature with higher viscosity so as to keep the hard candy layers from mixing too much. The form with the blue layer will make a product that has a washboard appearance. The final piece size is 2 grams, equally divided between the layers. The thickness of the product is less than one half of its width.

EXAMPLE 3

| Boiled Hard Candy | |
| --- | --- |
| First layer | |
| Isomalt | 99.48% |
| Peppermint flavor | 0.40% |
| Sweeteners | 0.12% |
| Total | 100.0 |
| Second layer | |
| Isomalt | 74.76% |
| Abrasive inclusions | 24.71% |
| Peppermint flavor | 0.40% |
| Blue color | 0.01% |
| Sweeteners | 0.12% |
| Total | 100.0 |

Isomalt is dissolved in an aqueous solution and boiled to about 1-3% moisture. This material is used as the first ingredient in both layers. As the solution is cooled, the flavor and sweetener are added, and the abrasive inclusions, which are granular maltitol, are added to the syrup used to make the second layer. The second layer can be deposited into the deposit form with a washboard surface on the bottom of the deposit form. This second layer can be deposited at a higher temperature to make it less viscous. The top or first layer can then be added to the deposit form at a lower temperature with higher viscosity so as to keep the hard candy layer from mixing too much. The form with the blue layer will make a product that has a washboard appearance. The product may be a 2 gram piece, evenly divided between the layers. The width of the product is at least 1.6 times the thickness of the product.

The abrasive inclusions can include encapsulated or entrapped flavors and colors. They can also be hard crystals of sugars or polyols. In Example 3 the abrasive inclusions are crystalline maltitol. The abrasive inclusions can also be other types of crystals, such as citric or malic acid, or other food acids that form hard crystals.

EXAMPLE 4

| Pressed Tablet | |
| --- | --- |
| First layer (white) | |
| Sorbitol | 98.11% |
| Intense sweeteners | 0.34% |
| Lemon/menthol flavor | 0.51% |
| Malic acid | 0.06% |
| Magnesium stearate | 0.98% |
| Total | 100.0 |
| Second layer (blue, fizzing) | |
| Sorbitol | 62.36% |
| Sodium bicarbonate | 19.96% |
| Malic acid | 16.21% |
| Intense sweeteners | 0.47% |
| Lemon/menthol flavor | 0.34% |
| Magnesium stearate | 0.62% |
| Blue color | 0.04% |
| Total | 100.0 |

For the first (white) layer, sorbitol, sweeteners, and acid were mixed for 5 minutes, flavor was added and mixed for 10 minutes, and then magnesium stearate was added and mixed for 2 minutes.

For the second (blue) layer, sorbitol, sweeteners, acid, bicarbonate, and color were mixed for 5 minutes, flavor was added and mixed for 10 minutes, and then magnesium stearate was added and mixed for 2 minutes.

Three parts of the white powder (about 0.66 grams) were placed in a die that included a mesh screen to form a rough surface, and tapped down. Two parts (about 0.44 grams) of blue powder were then poured into the die. The powders were compressed in the die, using about two metric tons of force. A two-layer whiteiblue tablet was formed. The blue layer was formed with an uneven surface conforming to the grids in the die. Those grids, along with crystals of the malic acid, provided an abrasive surface that scrubs the tongue. The product had a width to thickness ratio of about 1.84.

In this example, the sodium bicarbonate and malic acid are stable while in their solid form. However, when the product is placed in the mouth, these two ingredients start to dissolve and interact with one another, producing an effervescent action on the tongue.

EXAMPLES 5 A, B, D, E, G and H

A two layer pressed tablet was made according to the following formula.

| Layer 1 (bottom, scrubbing layer) | % |
|---|---|
| Sorbitol (Roquette Neosorb(TM)) | 65.94 |
| Palatinit Inclusions* | 32.97 |
| Magnesium Stearate | 0.49 |
| Peppermint Flavor | 0.49 |
| Aspartame | 0.07 |
| Acesulfame K | 0.02 |
| Cooling Agent (FEMA 4006) | 0.02 |
| | 100.00 |

*Palatinit (hydrogenated isomaltulose) particles with 0.30% food approved blue lake color sized to pass through a #20 sieve and be retained on a #40 sieve.

| Layer 2 (upper, smooth layer) | % |
|---|---|
| Sorbitol (Roquette Neosorb(TM)) | 98.91 |
| Magnesium Stearate | 0.49 |
| Peppermint Flavor | 0.49 |
| Aspartame | 0.07 |
| Acesulfame K | 0.02 |
| Cooling Agent (FEMA 4006) | 0.02 |
| | 100.00 |

Ingredients in the above formulas were dry blended together. A quantity of Layer 1 powder equal to 40% of the total piece weight was loaded into the die with lower punch (with tongue-cleaning features) inserted and compressed lightly by hand with the upper punch. The upper punch was removed and cleaned of loose powder. A quantity of Layer 2 powder equal to 60% of the total piece weight was loaded into the die/lower punch assembly on top of Layer 1 and compressed at 7000 pounds force to produce a bi-layer product having a lower, blue, tongue-cleaning layer with rough inclusions and a molded tongue-cleaning surface and an upper, white, generally smooth layer.

Pieces were formed using dies with upper and lower punches to produce shapes similar to some of those shown in the figures.

| | | Width/Thickness (in.) | Ratio |
|---|---|---|---|
| A. | FIGS. 17 and 18 | .458/.274 | 1.67 |
| B. | FIGS. 19 and 20 | .446/.252 | 1.77 |
| C. | Comparative Example C | .407/.259 | 1.57 |
| D. | FIGS. 25 and 26 | .566/.254 | 2.23 |
| E. | FIGS. 23 and 24 | .462/.287 | 1.61 |
| F. | Comparative Example F | .388/.256 | 1.52 |
| G. | FIGS. 27 and 28 | .559/.254 | 2.20 |
| H. | FIGS. 15 and 16 | .578/.256 | 2.26 |

Informal testing indicated that Examples D, G, and H (the FIG. 25/26 product, the FIG. 27/28 product and the FIG. 15/16 product) had the best resistance to "rolling" and were the easiest to manipulate with the tongue.

ADDITIONAL EXAMPLES

The Palatinit inclusions in the above examples are replaced with blue colored maltitol inclusions.

The Palatinit inclusions in the above examples are replaced with blue colored mannitol inclusions (Roquette Pearlitol 500DC™).

The confectionery tongue-cleaning product of Example 5 was repeated except that the Layer 1 (bottom scrubbing layer) was replaced with the following composition:

| Layer 1 (bottom, scrubbing layer) | % |
|---|---|
| Sorbitol (Roquette Neosorb(TM)) | 82.42 |
| Palatinit Inclusions* | 16.49 |
| Magnesium Stearate | 0.49 |
| Peppermint Flavor | 0.49 |
| Aspartame | 0.07 |
| Acesulfame K | 0.02 |
| Cooling Agent (FEMA 4006) | 0.02 |
| | 100.00 |

*same composition as in Ex. 5

The powder was used as before to prepare tablets using punches and die to produce the product illustrated in FIG. 23/24.

Some embodiments of the invention have a smooth upper surface so that the roof of the mouth and gums are not irritated by the product while the abrasive surface is used to scrub the tongue. An exemplary product has a small piece size so that it can be used discretely. The product can be used to scrub the tongue and other soft oral surfaces and remove odor causing bacteria while in public. By moving the specially formulated shape around in the mouth, the unique surface is designed to gently cleanse the mouth by lifting away the germs that cause bad breath in a way that the user can really feel. Clean and fresh breath, as well as other oral health benefits, are thus readily available. The products of the present invention provide an effective compliment to a daily oral care routine.

It should be appreciated that the products, processes and methods of the present invention are capable of being incorporated in the form of a variety of embodiments, only a few of which have been illustrated and described above. For example, other colors such as green may be used. The invention may thus be embodied in other forms without departing from its spirit or essential characteristics. It will be appreciated that the addition of some other ingredients, process steps, materials or components not specifically included will have an adverse impact on the present invention. The best mode of the invention may therefore exclude ingredients, process steps, materials or components other than those listed above for inclusion or use in the invention. However, the described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

The invention claimed is:

1. A confectionery product for use in cleaning the surface of a human tongue comprising:
   a) a first side and a second side generally opposite to said first side, and a product thickness, the first side comprising a hard surface;
   b) the second side comprising a hard, abrasive surface that is suitable for cleaning the top surface of a tongue within an oral cavity; and
   c) the second side having a width and a length, the smallest of which is at least 1.6 times the product thickness,
   d) wherein the product does not include a handle and wherein the product does not include a combination of a soft confectionery with a hard confectionery.

2. The confectionery product of claim 1 wherein the product has a size with no dimension greater than 25 mm.

3. The confectionery product of claim 1 comprising a pressed tablet.

4. The confectionery product of claim 1 comprising a deposited hard candy.

5. The confectionery product of claim 1 wherein the abrasive surface is provided at least in part by abrasive particles in the confectionery.

6. The confectionery product of claim 5 wherein the abrasive particles are embedded in only the surface layer of the abrasive surface.

7. The confectionery product of claim 1 wherein the abrasive surface comprises a formed, uneven surface.

8. The confectionery product of claim 7 wherein the confectionery forming the uneven surface also contains abrasive particles.

9. The confectionery product of claim 1 wherein the abrasive surface is provided at least in part by surface features having at least one scraping edge.

10. The confectionery product of claim 9 wherein the at least one scraping edge is located on a protrusion on the abrasive surface.

11. The confectionery product of claim 9 wherein the at least one scraping edge is formed on the edge of a groove in the abrasive surface.

12. The confectionery product of claim 1 wherein the abrasive surface is provided at least in part by surface features having a height of at least 0.018 inches.

13. The confectionery product of claim 1 wherein the abrasive surface is provided at least in part by surface features having a height of at least 0.020 inches.

14. The confectionery product of claim 1 wherein the product thickness is between about 1/16 and about 1/2 inch.

15. The confectionery product of claim 14 wherein the smallest of the length and width of the second surface is between about 1/4 and about 1 inch.

16. The confectionery product of claim 1 wherein the abrasive surface comprises a plurality of individual bumps protruding from the abrasive surface.

17. The confectionery product of claim 1 wherein the abrasive surface is generally planar except for the features making it abrasive.

18. The confectionery product of claim 1 wherein the abrasive surface is generally concave except for the features making it abrasive.

19. The confectionery product of claim 1 wherein the abrasive surface is generally convex.

20. The confectionery product of claim 1 wherein the abrasive surface includes a plurality of grooves.

21. The confectionery product of claim 1 wherein the product is generally circular in shape in plan view.

22. The confectionery product of claim 1 wherein the product is generally triangular in plan view.

23. The confectionery product of claim 1 wherein the second side is generally planar.

24. The confectionery product of claim 1 wherein the abrasive surface is provided at least in part by a plurality of generally parallel ridges extending generally across the second side.

25. The confectionery product of claim 1 wherein the product thickness is determined by forming an imaginary three dimensional box having three sets of two parallel sides, each side being at right angles to the other sides to which it is connected, two of the parallel sides being horizontal and considered as top and bottom sides, the sides each contacting the surface of the product and not intersecting the product, the product being oriented such that its center of gravity is a close as possible to the bottom side, the box having the smallest volume of any possible box meeting the forgoing criteria, the thickness being the smallest dimension of said box.

26. The confectionery product of claim 25 wherein the width and length of the second side are the other two dimensions of said box.

27. The confectionery product of claim 1 wherein the confectionery product includes one or more anti-bacterial agents.

28. The confectionery product of claim 27 wherein the anti-bacterial agent is selected from the group consisting of cardamom oil, magnolia bark extract, cranberry, geraniol, cinnamaldehyde, peppermint, triclosan, chlorhexidine, cetyl pyridinium chloride (CPC) and mixtures thereof.

29. The confectionery product of claim 1 wherein the confectionery product includes one or more physiological cooling agents.

30. The confectionery product of claim 29 wherein the physiological cooling agent is selected from the group consisting of menthol, N-2,3-trimethyl-2-isopropyl butanamide, 3-/-menthoxypropane-1,2-diol, N-ethyl-p-menthane-3-carboxamide, menthane ketals, menthyl succinate, isopulegol, menthyl glutarate and mixtures thereof.

31. The confectionery product of claim 1 wherein the confectionery product includes one or more breath freshening agents.

32. The confectionery product of claim 31 wherein the breath freshening agent is selected from the group consisting of salts of zinc, salts of copper, polyphenols, mushroom extracts and mixtures thereof.

33. The confectionery product of claim 1 wherein the confectionery includes one or more breath freshening and mouth odor masking flavors.

34. The confectionery product of claim 33 wherein the breath freshening and mouth odor masking flavor is selected from the group consisting of cinnamon, mint, wintergreen, fruit flavors and mixtures thereof.

35. The confectionery product of claim 1 wherein the confectionery product includes one or more dental active agents.

36. The confectionery product of claim 35 wherein the dental active agent is selected from the group consisting of tooth whiteners, fluoride, stain removers, calcium salts, phosphate salts and mixtures thereof.

37. The confectionery product of claim 5 wherein the abrasive particles comprise a material selected from the group consisting of crystalline sugars, crystalline polyols, solid matrices of carbohydrates, solid matrices of polyols, extruded carbohydrates, extruded polyols, granular food acids, granular inorganic salts and mixtures thereof.

38. The confectionery product of claim 1 wherein the product is generally cylindrical in shape with a height less than one-half the diameter of the cylinder, and the abrasive surface comprises at least one of the ends of the cylinder.

39. The confectionery product of claim 5 wherein the abrasive particles are of a different color than the confectionery in which they are contained.

40. The confectionery product of claim 5 wherein the abrasive particles also carry a flavor.

41. The confectionery product of claim 1 wherein the product thickness is at least about ⅛ inch.

42. The confectionery product of claim 15 wherein the greatest of the length and width of the second surface is less than 1 ½ inches.

43. The confectionery product of claim 1 wherein the product width is at least 1.7 times the product thickness.

44. The confectionery product of claim 1 wherein the product width is at least 1.8 times the product thickness.

45. The confectionery product of claim 1 wherein the product width is at least two times the product thickness.

46. The confectionery product of claim 1 wherein the first side comprises a domed shape, non-abrasive surface.

47. A confectionery product for use in cleaning the surface of a human tongue comprising:
 a) a first side and a second side generally opposite to said first side, and a product thickness;
 b) the second side comprising an abrasive surface that is suitable for cleaning the top surface of a tongue within an oral cavity; and
 c) the second side having a width and a length, the smallest of which is at least 1.6 times the product thickness,
 d) wherein the product does not include a handle, the product does not include a combination of a soft confectionery with a hard confectionery, and the product comprises a pressed tablet.

48. A confectionery product for use in cleaning the surface of a human tongue comprising:
 a) a first side and a second side generally opposite relative to said first side, and a product thickness, the first side comprising a domed shape, non-abrasive surface;
 b) the second side comprising an abrasive surface that is suitable for cleaning the top surface of a tongue within an oral cavity wherein
  i) the abrasive surface is generally convex,
  ii) the abrasive surface comprises a formed, uneven surface,
  iii) the confectionery forming the uneven surface also contains abrasive particles, and
  iv) the abrasive surface comprises a plurality of individual bumps protruding from the abrasive surface;
 c) the second side having a width and a length, the smallest of which is at least 1.6 times the product thickness, wherein the product thickness is determined by forming an imaginary three dimensional box having three sets of two parallel sides, each side being at right angles to the other sides to which it is connected, two of the parallel sides being horizontal and considered as top and bottom sides, the sides each contacting the surface of the product and not intersecting the product, the product being oriented such that its center of gravity is a close as possible to the bottom side, the box having the smallest volume of any possible box meeting the forgoing criteria, the thickness being the smallest dimension of said box, and wherein the width and length of the second side are the other two dimensions of said box;
 d) wherein the product is generally elliptical in shape in plan view and has a size
  i) with no dimension greater than 25 mm,
  ii) a product thickness of between about ⅛ and about ½ inch, and
  iii) the smallest of the length and width of the second surface is between about ¼ and about 1 inch, and
 e) wherein the product does not include a handle, the product does not include a combination of a soft confectionery with a hard confectionery, and the product comprises a pressed tablet and the confectionery includes one or more fruit flavors.

49. The confectionery product of claim 48 wherein the abrasive particles predominantly have particle sizes of between about 100 microns and about 2000 microns.

50. The confectionery product of claim 48 wherein the abrasive surface is provided at least in part by surface features having a height of at least 0.015 inches.

* * * * *